(12) United States Patent
Xiao et al.

(10) Patent No.: US 8,053,470 B2
(45) Date of Patent: Nov. 8, 2011

(54) PROCESS FOR THE PREPARATION OF POLYNUCLEAR FERRIC HYDROXIDE-SACCHARIDE COMPLEXES

(75) Inventors: Jinmai Xiao, Chongqing (CN); Jie Deng, Chongqing (CN); Jinhua Feng, Chongqing (CN); Bo Xiao, Chongqing (CN)

(73) Assignee: Chongqing Pharmaceutical Research Institute Co., Ltd., Chongqing (CN)

( * ) Notice: Subject to any disclaimer, the term of this patent is extended or adjusted under 35 U.S.C. 154(b) by 1004 days.

(21) Appl. No.: 11/911,449

(22) PCT Filed: Apr. 12, 2006

(86) PCT No.: PCT/CN2006/000655
§ 371 (c)(1),
(2), (4) Date: Oct. 12, 2007

(87) PCT Pub. No.: WO2006/114040
PCT Pub. Date: Nov. 2, 2006

(65) Prior Publication Data
US 2008/0176941 A1  Jul. 24, 2008

(30) Foreign Application Priority Data
Apr. 26, 2005  (CN) .......................... 2005 1 0025417

(51) Int. Cl.
*A61K 31/295* (2006.01)
(52) U.S. Cl. ...................................... 514/502
(58) Field of Classification Search ............... 514/502
See application file for complete search history.

(56) References Cited

U.S. PATENT DOCUMENTS

| | | | | |
|---|---|---|---|---|
| 3,686,397 A * | 8/1972 | Muller | ............................ | 514/58 |
| 3,794,722 A | 2/1974 | Taya | | |
| 6,537,820 B2 | 3/2003 | Beck et al. | | |
| 2003/0216566 A1 | 11/2003 | Kumari et al. | | |

FOREIGN PATENT DOCUMENTS

| CN | 1097989 A | | 2/1995 |
|---|---|---|---|
| DE | 3844065 A1 | | 7/1990 |
| EP | 1 756 132 | | 2/2007 |
| IN | 187116 A | | 1/2000 |
| IN | 187116 | * | 2/2002 |
| RU | 2198665 CI | | 2/2003 |
| WO | 2005/000210 | | 1/2005 |
| WO | 2005/094202 | | 10/2005 |
| WO | 2005/116040 A1 | | 12/2005 |
| WO | 2006/006185 | | 1/2006 |

OTHER PUBLICATIONS

Nissim et al, The Lancet, 1949, 23, 686-89.*
USP "Iron Sucrose Injection" United States Pharmacopeia and National Formulary (USP27-NF22) 2004, pp. 1025-1029.
National Kidney Foundation K/DOQI Guidelines, KDOQI Clinical Practice Guidelines and Clinical Practice Recommendations for Anemia in Chronic Kidney Disease, pp. 1-21, 2006.
Venofer, pp. 1-9, 1997.
Geisser, et al., "Structure / Histotoxicity Relationship of Parental Iron Preparations," Arzneim.-Forsch./Drug Res., 42 (II), No. 12, (1992), pp. 1439-1452.
Iron Sucrose Injection, pp. 5, 2008.
Nissim, et al., "Preparation and Standardisation of Saccharated Iron Oxide for Intravenous Administration," The Lancet, Apr. 23, 1949, pp. 686-689.

* cited by examiner

Primary Examiner — Shaojia Anna Jiang
Assistant Examiner — Ganapathy Krishnan
(74) Attorney, Agent, or Firm — Workman Nydegger

(57) ABSTRACT

The invention discloses a process for preparing a polynuclear ferric hydroxide-saccharide complex, including: adding an aqueous solution of an alkaline substance drop-wise into an aqueous solution of iron salt at a temperature of 5-20° C. until pH 6-8, collecting the polynuclear ferric hydroxide from the reaction mixture by a conventional method; reacting the polynuclear ferric hydroxide with a saccharide in a solution of an alkaline substance for 10-40 hours at 106-125° C. under pH 10-12, resulting in a crude product having an isoelectric point of 4.4-5.3 and a weight average molecular weight of 20,000-100,000 Daltons, and then harvesting the polynuclear ferric hydroxide-saccharide complex from the crude product. The process can precisely control the molecular weight of the polynuclear ferric hydroxide-saccharide complex without an effect on the other characteristics of the product, for example its saccharide content or isoelectric point etc. Furthermore, it is very simple and readily applicable in industry.

11 Claims, No Drawings

PROCESS FOR THE PREPARATION OF POLYNUCLEAR FERRIC HYDROXIDE-SACCHARIDE COMPLEXES

FIELD OF THE INVENTION

The invention relates to a method for preparing a polynuclear ferric hydroxide-saccharide complex, especially a method which can be used to prepare a polynuclear ferric hydroxide-saccharide complex with a controllable molecular weight and isoelectric point.

BACKGROUND OF THE INVENTION

Iron-deficiency anemia is referred to as microcytic hypochromic anemia, one of the most popular anemia throughout the world, which is caused by insufficient iron storage in the body to an extent that affects the synthesis of hemoglobin.

Iron deficiency may be caused by various factors, such as insufficient iron intake, increased iron consumption, excessive loss of iron, poor absorption of iron, or increased loss of free iron, etc. The most effective way for treating iron deficiency anemia is to replenish iron. The way of replenishing iron comprises oral iron supplementation which are generally iron salts of a small molecular weight, such as ferrous sulfate, ferrous gluconate, ferrous lactate and the like; or parenteral iron which are typically complexes of iron and a saccharide, including polysaccharide, oligosaccharide, or monosaccharide, such as iron dextran, iron sucrose (published in the current USP and the Chinese Pharmacopoeia), and sodium ferric gluconate, due to their good solubility and relatively low toxicity upon parenteral administration.

Although oral administration of iron is the major way for iron replenishment, sometimes it is especially advantageous to parenteral iron supplementation, for example, when oral administration of iron is inappropriate, oral iron therapy is ineffective, or there is an urgent need of rapidly correcting iron deficiency anemia. In particular, parenteral iron is being used more and more often to replace oral administration in treating renal anemia. As reported in the clinical practice guidelines for the treatment of anemia of chronic renal failure made by the U.S. National Kidney Foundation Dialysis Outcome Quality Initiative, NKF-DOQI in 1997: "When Epoetin is administered to a patient of chronic kidney dysfunction (CKD), it is necessary to maintain the value of Ht to 33-36% (corresponding to a level of Hb of 11-12 g/dl), thus supplemental iron should be administered to prevent iron deficiency and to maintain adequate iron storage. Oral administration of iron cannot maintain a sufficient level of iron in adult patients before hemodialysis, home hemodialysis patients, and peritoneal dialysis (PD) patients in vivo. Iron may be orally administered to a hemodialysis patient, but it is unlikely for the patient to maintain a TSAT of above 20%, serum ferritin at a level higher than 100 ng/mL, and an Ht value of 33% to 36% (an Hb level of 11 to 12 g/dL). To achieve and maintain an Ht value of 33% to 36% (an Hb level of 11 to 12 g/dL), most hemodialysis patients will require intravenous iron injection on a regular basis." However, the use of iron dextran will cause dosage-independent allergic response (0.7%-1%) that even seriously threatens the lives of patients. In 1991-1999, more than 30 patients died of allergic responses to iron dextran. While, the incidence rate of severe allergy caused by administration of iron sucrose and sodium ferric gluconate is apparently lower than that caused by administration of iron dextran. Among 450,000 patients who had been treated with iron sucrose injection of the trade name of Venofer® during 1992-1999, 27 cases were reported to exhibit an allergic reaction, of which only 8 cases were serious (http://www.h-cfa.gov/coverage/8b3-11.htm), thus iron dextran is gradually being replaced by iron sucrose.

The polynuclear ferric hydroxide-saccharide complexes being referred to herein do not include complexes of high molecular weight polysaccharide such as dextran and ferric hydroxides, unless specifically indicated otherwise in the context.

Iron sucrose is a polynuclear ferric hydroxides-sucrose complex having a high molecular weight, and the relative molecular weight Mw (weight-average molecular weight) of a commercially available product (Venofer®) is 34000-60000 Daltons. Some literatures reported that the molecular weights of iron-saccharide complexes are relevant to their pharmacodynamic parameters and side effects such as allergy during their clinic application. If their molecular weights are too high or too low, they will cause adverse effects. Therefore, for such iron-saccharide complexes, it is quite important to control their molecular weight within a suitable range so as to ensure the safety and effectiveness in their clinical application as well as the quality homogeneity of the product. The specifications for iron sucrose injection is recorded in the $27^{th}$ version of USP, which species the range of the relative molecular weight of iron sucrose (Mw 34000-60000 Daltons, Mw/Mn<1.7, Mn being the number-average molecular weight) and methods for the determination thereof.

However, although the iron sucrose has been marketed for many years, there are few reports on its preparation methods. Nissim (The Lancet Apr. 23, 1949 p 686-689) disclosed a method for preparing iron sucrose, and mentioned the control of the isoelectric point of iron sucrose. It demonstrated that the toxicity of iron sucrose increased when the isoelectric point was too high or too low, yet it did not mention the control of the molecular weight thereof. In the specifications for iron sucrose injection liquid embodied in $27^{th}$ version of USP, the isoelectric point is specified as 4.4-5.3.

Patent publication No. WO 2005000210 described a method for preparing an iron-saccharide complex with an absolute molecular weight of above 25,000 Daltons, wherein an aqueous solution or dispersion containing iron ions and hydroxyl ions is heated together with a saccharide under an alkaline condition for a given time to allow the iron-saccharide complex to reach a desired molecular weight. However, except that the absolute molecular weight of the resulting complex was determined therein, the preparation process disclosed therein has no significant difference from that recited in the published literatures. Neither did WO 2005000210 disclose how to control the molecular weight of the complex more accurately or how to control its isoelectric point. Therefore, those skilled in the art can neither produce products which meet the requirements of the USP nor ensure the safety of the products in accordance with the techniques disclosed in WO 2005000210.

In the published patent application No. WO 2005000210, the molecular weight of the iron-saccharide complex is controlled by heating a mixture of iron and a saccharide under an alkaline condition for a given time until a desired molecular weight is reached. Specifically, WO 2005000210 teaches that, where the molecular weight of the complex is higher than that desired, excess saccharide may be added to lower it. However, this is disadvantageous during the drug manufacturing process because the addition will change the content of the saccharide in the product, which has to be restricted to a specific range, for example, from 26% to 34% as stipulated in the $27^{th}$ version of USP. Apparently, the method as disclosed in WO 2005000210 has a limited ability to control the range of the molecular weight of the product. Furthermore, in WO 2005000210, it is also mentioned that, when the iron-saccharide mixture is heated to a temperature of aggregation-point, the molecular weight of the product will tend to increase or decrease over time depending on the difference in the content of the saccharide in the product. Clearly, it will be difficult for the process to be used for preparing an iron-saccharide complex with a high molecular weight when the content of the saccharide is high.

SUMMARY OF THE INVENTION

The first technical problem to be solved in the present invention is to disclose a method for preparing a polynuclear ferric hydroxide-saccharide complex with a controllable molecular weight and isoelectric point, thereby overcoming the defects of incapability to precisely control the relative molecular weight and isoelectric point of the product, and thus meet the demands in the art.

The second technical problem to be solved in the present invention is to disclose a polynuclear ferric hydroxide for preparing said polynuclear ferric hydroxide-saccharide complex.

The technical concept of the present invention lies in the following finding:

Where the saccharide that takes part in the reaction is a saccharide of a small molecular weight, such as monosaccharide or disaccharide, the key step of precisely controlling the final molecular weight of the iron-saccharide complex is not the step of aggregating or compounding ferric hydroxide with saccharide as believed before.

Generally, when preparing an iron-saccharide complex, one protocol is to prepare ferric hydroxide firstly and then react it with a saccharide under a certain condition; another protocol comprises preparing ferric hydroxide in situ, and then reacting it directly with a saccharide. In technical literatures reported previously, for example in WO2005000210, it is mentioned that hydroxides or hydrated oxides could be prepared at any temperature between 20-75° C., but there is no teaching of any effects of the reaction conditions for preparing hydroxide, for example the temperature, on the molecular weight of the resulting iron-saccharide complex. In this application, however, the present inventors found out that the conditions for preparing ferric hydroxide significantly affect the final molecular weight of the resultant iron-saccharide complex, to an extent far larger than that of the conditions for compounding/aggregating ferric hydroxide with a saccharide.

Polynuclear ferric hydroxide is generally prepared by neutralizing an iron salt with an alkaline substance. At a relatively low pH, mononuclear hydrates of ferric hydroxide, for example $Fe(OH)^{2+}$, $Fe(OH)_2^+$, are formed, while as the pH increases, polynuclear hydrates of ferric hydroxide, i.e. the aggregation of multiple iron atoms, are gradually formed. It can be seen from prior art literatures that the hydrolysis of iron salts is very complicated, being affected by various factors such as the concentration of the reactants, the reaction temperature, the aging time, the drop-wise addition time, the kind and amount of the alkaline substance, and pH etc. Different conditions will result in different hydrolysis products, thereby endowing different properties to the final iron-saccharide complex. In recent studies, it is found that structurally iron-saccharide complex is a macromolecular complex, which is composed of "iron nucleus" formed from inner polynuclear ferric hydroxide non-covalently linked to the external "shell" formed from carbohydrate such as sucrose. The size and shape of the iron nucleus will largely affect the molecular weight of the iron-saccharide complex formed thereby. The present inventors' experiments showed that the molecular weight of the final iron-saccharide complex changed by more than 20,000 Dalton when the temperature at which ferric hydroxide was prepared varied by only 5° C. For the production of an iron-saccharide complex within a narrow molecular weight range, such as 34,000-60,000 Daltons, the conditions for preparing polynuclear ferric hydroxide have to be strictly controlled so as to ensure the quality stability among batches of the products.

Under the above concept, the present invention provides a method, comprising the steps of:
(1) preparing polynuclear ferric hydroxide; and
(2) reacting the polynuclear ferric hydroxide with a saccharide under an alkaline condition to obtain said polynuclear ferric hydroxide-saccharide complex;

characterized in that the preparing of the polynuclear ferric hydroxide comprises the following steps: an aqueous solution of an alkaline substance was added drop-wise into an aqueous solution of an iron salt at a temperature of 5-20° C., during which a large amount of carbon dioxide were generated, and the color of the solution changed from light brown to dark brown, until the pH reached an end point of 6 to 8, then collecting the polynuclear ferric hydroxide from the reaction mixture through a conventional method.

The reaction between the polynuclear ferric hydroxide with the saccharide needs just conventional techniques, which have been disclosed in a number of prior art documents; therefore it will not be described in detail herein. Those skilled in the art can conduct the reaction according to the method disclosed in Nissim (The Lancet Apr. 23, 1949 p 686-689);

In one embodiment, the reaction temperature preferably is 10-17° C.;

In another embodiment, the time for the drop-wise addition is from 1 min to 5 h, preferably 25-35 min;

In a further embodiment, said iron salt is selected from the group being consisted of $FeCl_3.6H_2O$, $FeCl_3$, ferric sulfate or ferric nitrate, or mixtures thereof, preferably $FeCl_3.6H_2O$;

In yet another embodiment, said alkaline substance is selected from the group being consisted of carbonate of alkali metals, bicarbonate of alkali metals, hydroxide of alkali metals, and hydroxide of alkaline earth metals;

In yet another embodiment, preferably the alkaline substance is sodium carbonate, sodium bicarbonate, sodium hydroxide, and potassium hydroxide;

In yet another embodiment, the concentration of the aqueous solution of said alkaline substance is 5-25% by weight, preferably a saturated aqueous solution of said alkaline substance;

In yet another embodiment, the concentration of the aqueous solution of said iron salt is 5-50% by weight;

In accordance with the preferred embodiments of the present invention, the variation of the temperature during the reaction is not too broad, but controlled within the range of 5° C., preferably within 2° C.;

In the present invention, the temperature for preparing polynuclear ferric hydroxide is controlled between 5-20° C. When the temperature increases, the molecular weight of the final iron-saccharide complex will increase as well. When the temperature is above 20° C., the variation of the temperature will affect the molecular weight of the resulting iron-saccharide complexes vastly, such that it is very difficult to control the industrial production and to ensure the quality uniformity among batches of products. The molecular weight of the iron-saccharide complex is also affected significantly by the speed of the drop-wise addition of the component. The faster the speed, the lower the molecular weight of the final iron-saccharide will be, and vice versa. Considering the operability in industrial production as well as the above-mentioned temperature control, the time for the drop-wise addition may be within the range from 1 min. to 5 h, preferably 30±5 min. After the neutralization is completed, precipitates of polynuclear ferric hydroxide may be obtained by filtration, centrifugation or sedimentation, which can be washed by water to remove side-products such as NaCl, and then used in subsequent reactions.

As described above, the mixture of the resultant polynuclear ferric hydroxide and a saccharide can be heated under an alkaline condition by a conventional method, resulting in a polynuclear ferric hydroxide-saccharide complex with a predetermined molecular weight.

However, the present inventor found out that the isoelectric point of the final polynuclear ferric hydroxide-saccharide complex could be controlled within the range of 4.4-5.3 through controlling the temperature and duration of the reaction between ferric hydroxide and a saccharide, without any effect on the molecular weight of the obtained product.

The term "isoelectric point" herein refers to a pH value at which the aqueous solution of iron-saccharide complexes turns turbid during the drop-wise addition of a diluted hydrochloric acid solution. This value is relevant to the toxicity of the complex. Specifically, human plasma is at a pH of about 7, thus where the isoelectric point of the iron-saccharide complex is from 5.5 to 7, the complex will precipitate in the blood vessels, resulting in severe consequences. In the 27$^{th}$ version of USP, it is stipulated that the isoelectric point of iron-sucrose injection liquid should be within the range of 4.4-5.3. Therefore, the reaction must be strictly controlled to ensure the isoelectric point of products being within this range. If the reaction of iron-saccharide mixture is carried out at a relatively low temperature for example lower than 100° C. for a short time such as 2 h, then the isoelectric point of the resultant iron-saccharide complex generally is about pH6-7.

Therefore, the method of the present invention for preparing the product of interest from the polynuclear ferric hydroxide as obtained above and a saccharide under an alkaline condition comprises the steps of:
reacting ferric hydroxide with a saccharide in an alkaline solution for 10-30 h at a pH of 9-12 and a temperature of 106-125° C., so as to obtain a crude product with an isoelectric point of pH4.4-5.3, then collecting the final product of iron-saccharide complex from the reaction mixtures.

The weight-average molecular weight of the above complex as measured by gel permeation chromatography GPC is 50,000 Daltons.

In one embodiment, said saccharide is selected from the group being consisted of monosaccharides, disaccharides and mixtures thereof;

In another embodiment, said monosaccharide is selected from the group being consisted of fructose, glucose and mannose;

In yet another embodiment, said disaccharide is selected from the group being consisted of sucrose, maltose and trehalose;

In a further embodiment, the saccharide is preferably sucrose;

In a still further embodiment, said alkaline solution is an aqueous solution of hydroxides of alkali earth metals or alkali metals, preferably one of the aqueous solutions of sodium hydroxide and potassium hydroxide.

By employing the preparation process of the present invention, products of polynuclear iron-saccharide complex can be obtained, which have any desired weight-average molecular weight within the range of 20,000-100,000 Daltons, the difference of the molecular weights between each batch being controlled within ±5,000 Daltons, and the isoelectric point being controlled within 4.4-5.3. The weight ratio of ferric hydroxide and the saccharide in the complex is 1:18-1:13, the content of iron therein is 1-10%, and the water content is <10%.

It can be seen from the technical solution disclosed above that, the method of the present invention has solved the technical problem of precisely controlling the molecular weight of the polynuclear ferric hydroxide-saccharide complex and overcome the conventional technical prejudice, without affecting other features of the products such as the saccharide contents, their isoelectric point, and the like. The method of the present invention can be conveniently operated and carried out in industrial scale.

DETAILED DESCRIPTION OF THE INVENTION

Example 1

Preparation of Polynuclear Ferric Hydroxide:

50 g of $FeCl_3.6H_2O$ were added into a beaker of 2 L volume, and 0.5 L of distilled water was added thereto, then the mixture was agitated to dissolve the solid. The temperature was kept at 15° C., and a saturated solution of sodium carbonate was added drop-wise with stirring, during which a large amount of carbon dioxide was generated, and the color of the solution changed from light brown to dark brown. The drop-wise addition was continued for 32 minutes, then stopped once the reaction reached its end point at pH 7. During the reaction, the fluctuation of the temperature was controlled within 5° C.

Refining of Polynuclear Ferric Hydroxide:

The above suspension was centrifuged. The precipitates were placed in a beaker of 3 L, and washed with 2 L of distilled water under stirring for 40 minutes, and then centrifuged again. The washing procedures were repeated totally 4 times. The final brown precipitates were tested for their contents of iron and chlorides, and then immediately used in the next reaction after proving to be qualified.

Preparation of Polynuclear Ferric Hydroxide-sucrose Complex:

The above-prepared precipitate was added into a beaker of 500 mL, then 166 g of sucrose and 30 mL of 20% (w/v) aqueous sodium hydroxide solution were added. The reaction was performed at a temperature of 106° C. and a pH of 12 for 25 h. Then the reaction was stopped, a crude product was obtained and filtered. The filtrate was spray dried to give a brown powdery final product.

The weight average molecular weight of the final product was 50,000 Daltons as measured by gel chromatography GPC.

As measured by the method disclosed in the part of the 27$^{th}$ version of USP concerning the quality standards of iron sucrose injection liquid, the isoelectric point of the final product was 4.4. The weight ration of iron to sucrose was 1:16, with the iron content being 5.5% and the water content being 8%.

Examples 2-6

In these examples, 5 different reaction conditions were compared, which were the same as that of example 1 except for the temperature for preparing the ferric hydroxide. The results were shown in the following table.

| example | Temperature for preparing Fe(OH)$_3$ (°C.) | Weight average molecular weight (Daltons) | Isoelectric point | Weight ratio of iron to saccharide % | Iron content % |
|---|---|---|---|---|---|
| 2 | 5 | 24,000 | 4.8 | 1:15 | 5.2 |
| 3 | 10 | 30,000 | 4.7 | 1:14 | 5.6 |
| 4 | 15 | 48,000 | 5.0 | 1:15.5 | 6 |
| 5 | 20 | 80,000 | 4.5 | 1:16 | 5 |
| 6 | 25 | 150,000 | 4.6 | 1:17 | 5.3 |

It can be seen from the above results that the temperature for preparing ferric hydroxide has a significant influence on the molecular weight of the resulting iron-saccharide complex, and products with a desired molecular weight can be obtained through strict control of the temperature.

Examples 7-10

5 reaction conditions were compared, which are the same to that of example 1 except for that listed below.

| example | Duration for the addition (min.) | The temperature for preparing ferric hydroxide (°C.) | The temperature of the reaction between iron and saccharide (°C.) | Weight-average molecular weigh (Dalton) | Duration of the reaction between iron and saccharide (h) | Isoelectric point |
|---|---|---|---|---|---|---|
| 7 | 32 | 15 ± 2 | 80 | 54,000 | 36 | 5.8 |
| 8 | 30 | 15 ± 2 | 100 | 50,000 | 36 | 5.4 |
| 9 | 30 | 15 ± 2 | 110 | 48,000 | 16 | 4.8 |
| 10 | 31 | 15 ± 2 | 120 | 47,000 | 13 | 4.7 |

It can be seen from the above results that iron-saccharide complex with good uniformity among batches can be obtained through strict control of the temperature for preparing ferric hydroxide and the duration for the drop-wise addition of the component. The conditions of the reaction between the iron hydroxide and the saccharide slightly affect the molecular weigh of the complex, but significantly affect the isoelectric point of the complex. Under a temperature of below 100° C., the isoelectric point of the resulting complex will not be lower than 5.3 even when the period for the reaction is extended.

Example 11

Preparation of Polynuclear Ferric Hydroxide:

25 g of ferric sulfate and 30 g of ferric nitrate were added into a 2 L beaker, then 0.4 L of distilled water was added to dissolve the solids under stirring. The temperature was kept at 15° C., and 30 wt % aqueous solution of sodium hydroxide was added drop-wise under stirring, during which a large amount of carbon dioxide was generated, with the color being changed from light brown to dark brown. The addition was continued for 15 minutes, then stopped when the reaction reached its end point of pH 7.1, with the temperature fluctuation being controlled within 2° C. during the reaction.

Refining of Polynuclear Ferric Hydroxide:

The above suspension was centrifuged, then the precipitate was placed in a 3 L beaker and washed with 2 L of distilled water for 40 minutes under stirring, and centrifuged again; the washing procedure was repeated for a total of 4 times. The final brown precipitates were tested for their contents of iron and chlorides, and then immediately used in the next reaction after proving to be qualified.

Preparation of Polynuclear Ferric Hydroxide-fructose Complex:

The precipitate as prepared above was added into a beaker of 500 mL, then 160 g of fructose and 30 mL of 20% (w/v) sodium hydroxide solution were added. The reaction was conducted at a temperature of 125° C. under pH 10 for 10 hours. Then the reaction was stopped and the crude product was harvested, filtered, and the filtrate spray dried to give a brown powdery final product.

The isoelectric point of the above final product is 5.2, with the weight-average molecular weight being 30,000 Daltons, the iron content being 10%, and the water content being 5%.

What is claimed is:

1. A method for preparing a ferric-saccharide complex, comprising:
   (1) preparing a polynuclear ferric hydroxide;
   (2) reacting said ferric hydroxide with a saccharide under an alkaline condition;
   wherein preparing the polynuclear ferric hydroxide includes:
      adding an aqueous solution of an alkaline substance drop-wise into an aqueous solution of iron salt at a temperature of 5-17° C., until the reaction reaches its end point of pH 6-8, then separating and collecting the polynuclear ferric hydroxide from the reaction mixture; and
   wherein reacting said polynuclear ferric hydroxide with saccharide under an alkaline condition comprises:
      reacting the polynuclear ferric hydroxide with a saccharide in an alkaline solution at a temperature of 106-125° C. under pH 9-12 for 10-30 hours, then collecting iron saccharide complex final product from the reaction mixture.

2. A method according to claim 1, wherein the duration for the drop-wise addition of the component is 1 min. to 5 h.

3. A method according to claim 1, wherein the duration for the drop-wise addition of the component is 25 to 35 min.

4. A method according to claim 1, wherein said iron salt is selected from the group consisting of FeCl$_3$.6H$_2$O, FeCl$_3$, ferric sulfate or ferric nitrate, or any combination thereof.

5. A method according to claim 1, wherein said alkaline substance is selected from the group consisting of carbonate of alkali metals, bicarbonate of alkali metals, hydroxide of alkali metals, or hydroxide of alkaline earth metals.

6. A method according to claim 1, wherein said alkaline substance is selected from the group consisting of sodium carbonate, sodium bicarbonate, sodium hydroxide, and potassium hydroxide, preferably sodium carbonate.

7. A method according to claim 1, wherein the fluctuation of the temperature during the reaction is controlled within 5° C.

8. A method according to claim 1, wherein said alkaline solution is an aqueous solution of hydroxide of alkaline earth metal or hydroxide of alkali metal, preferably an aqueous solution of sodium hydroxide.

9. A method according to claim 1, wherein the concentration of the iron salt aqueous solution is 5-50% by weight.

10. A method according to claim 1, wherein said saccharide is selected from the group consisting of monosaccharides, disaccharides, or mixtures thereof.

11. A method according to claim 10, wherein said saccharide is selected from the group consisting of fructose, glucose, mannose, sucrose, maltose and trehalose, or mixtures thereof.

* * * * *

UNITED STATES PATENT AND TRADEMARK OFFICE
CERTIFICATE OF CORRECTION

PATENT NO. : 8,053,470 B2  Page 1 of 1
APPLICATION NO. : 11/911449
DATED : November 8, 2011
INVENTOR(S) : Xiao et al.

It is certified that error appears in the above-identified patent and that said Letters Patent is hereby corrected as shown below:

Title Page, Item 54, Left Hand Column
Line 3, change "HYDROXIDE-SACCARIDE" to --HYDROXIDE-SACCHARIDE--

Column 1
Line 3, change "HYDROXIDE-SACCARIDE" to --HYDROXIDE-SACCHARIDE--

Column 2
Line 9, change "hydroxides-sucrose" to --hydroxide-sucrose--
Line 35, change "in 27$^{th}$ version" to --in the 27$^{th}$ version--

Column 4
Line 20, change "were" to --was--
Line 55, change "2° C.;" to --2° C.--

Column 6
Line 38, change "totally 4" to --a total of 4--
Line 58, change "ration" to --ratio--

Column 7
Line 41, change "weigh" to --weight--

Signed and Sealed this
Twentieth Day of March, 2012

David J. Kappos
*Director of the United States Patent and Trademark Office*